United States Patent [19]

Martella

[11] Patent Number: 4,632,674
[45] Date of Patent: Dec. 30, 1986

[54] DIESEL FUEL CONTAINING A TETRAZOLE OR TRIAZOLE CETANE IMPROVER

[75] Inventor: David J. Martella, Plainsboro, N.J.

[73] Assignee: Exxon Chemical Patents Inc., Linden, N.J.

[21] Appl. No.: 813,988

[22] Filed: Dec. 27, 1985

[51] Int. Cl.$^4$ .............................................. C10L 1/10
[52] U.S. Cl. .......................................... 44/57; 44/63; 44/64; 548/250
[58] Field of Search ................ 44/57, 63, 64; 548/250

[56] References Cited

U.S. PATENT DOCUMENTS

| | | | |
|---|---|---|---|
| 1,943,148 | 1/1934 | Scheuing et al. | 260/44 |
| 2,225,879 | 12/1940 | Miller et al. | 44/9 |
| 2,316,011 | 4/1943 | Miller et al. | 44/57 |
| 2,507,337 | 5/1950 | Harvill et al. | 260/308 |
| 2,934,048 | 4/1960 | Young | 123/1 |
| 2,977,372 | 3/1961 | Finnegan et al. | 260/308 |
| 3,261,844 | 7/1966 | Trofimenko | 44/63 |
| 3,288,802 | 11/1966 | Bobinski | 44/64 |
| 3,437,665 | 4/1969 | Maggiulli et al. | 260/308 |
| 3,511,623 | 5/1970 | Patinkin | 44/63 |
| 4,294,585 | 10/1981 | Sung | 44/53 |
| 4,421,522 | 12/1983 | Seemuth | 44/53 |
| 4,445,907 | 5/1984 | Sung | 44/53 |
| 4,457,763 | 7/1984 | Seemuth | 44/57 |
| 4,511,368 | 4/1985 | Knapp | 44/63 |
| 4,518,782 | 5/1985 | Sung et al. | 44/63 |

Primary Examiner—William R. Dixon, Jr.
Assistant Examiner—Margaret B. Medley
Attorney, Agent, or Firm—R. A. Maggio

[57] ABSTRACT

There is disclosed a diesel fuel containing a cetane number improving additive such as 5-propyl-1,2,3,4-tetraazacyclopenta-2,4-diene.

7 Claims, No Drawings

DIESEL FUEL CONTAINING A TETRAZOLE OR TRIAZOLE CETANE IMPROVER

BACKGROUND OF THE INVENTION

The present invention relates to diesel fuel compositions containing certain azole compounds as cetane improvers.

Diesel engines operate by compression ignition. They have compression ratios in the range of 14:1 to 17:1 or higher and for that reason obtain more useful work from a given amount of fuel compared to an Otto cycle engine. Historically, diesel engines have been operated on a petroleum-derived liquid hydrocarbon fuel boiling in the range of about 300°–700° F. Recently, because of dwindling petroleum reserves, alcohol-hydrocarbon blends have been studied for use as diesel fuel.

The ignition quality of diesel fuels is expressed in terms of "cetene" or "cetane" numbers, which numbers have been developed on a basis very similar to that adopted for measuring the ignition quality of gasoline in terms of octane numbers.

The cetene number refers to a mixture of cetene (1-hexadecene) and alpha-methylnaphthalene, whereas the cetane number refers to a similar mixture of cetane (n-hexadecane) and alpha-methylnaphthalene. The cetene or cetane numbers indicate volumetric percentages of cetene or cetane in the blend. Cetane is normally used because cetene is difficult to purify and is somewhat unstable in storage. Typically, a fuel consumption is assigned a cetane number by matching the ignition performance of a test sample with reference blends of cetane and alpha-methylnaphthalene. The volume percent of cetane in the blend which gives the same ignition quality test performance as the fuel test sample is taken as the cetane number of that fuel.

Cetane number is related to ignition delay after the fuel is injected into the combustion chamber. If ignition delays too long, the amount of fuel in the chamber increases and upon ignition results in a rough running engine and increased smoke. A short ignition delay results in smooth engine operation and decreases smoke.

Petroleum-derived distillate fuels in the diesel boiling range, without any cetane improver, generally have cetane numbers in the range of about 25–60. Cetane numbers in the range of 25–35 are considered low and those in the range of 50–60 are considered top grade diesel fuels. Diesel fuels in the 35–50 mid-range are most common. An object of the invention is to upgrade the low cetane number fuels at least into the mid-range and to increase the cetane value of the mid-range fuels into the upper portion of the mid-range (e.g., 45–50) or even into the premium range above 50.

Through the years, many types of additives have been used to raise the cetane number of diesel fuel. These include peroxides, nitrites, nitrates, nitrosocarbamates, and the like.

More specifically, U.S. Pat. No. 2,934,048 discloses alkyl nitrates such as amyl nitrate and hexylnitrate as cetane improvers.

Other nitrate cetane improvers for diesel fuels, such as dioxane nitrate and 4-morpholine ethanol nitrate, are disclosed in U.S. Pat. Nos. 4,457,763 and 4,421,522, respectively.

The use of alicyclic diazoacetates; di-azo-acetoacetic esters; diazo-acetic acid salts, iso-diazo-acetic esters, and bis diazo-acetic acid esters and salts, as diesel fuel cetane improvers is disclosed in U.S. Pat. No. 2,225,879.

U.S. Pat. No. 2,316,011 discloses organic compounds containing a five-membered heterocyclic ring structure containing both nitrogen and sulfur, such as, 1,2,3,4-thiatriazole; and 1,2,3,-thiadiazole, as cetane improvers for diesel fuels.

U.S. Pat. No. 3,511,623 discloses the use of metal salts of certain azoles as an additive for leaded gasolines. Suitable azoles from which the salts are prepared include aromatic and/or aliphatic hydrocarbon substituted or unsubstituted cyclopenta diazoles, triazoles, and tetrazoles. Such additives are disclosed to improve gasoline engine performance with respect to one or more of octane improvement, rumble, surface ignition characteristics, piston ring wear, and exhaust valve life. As is well known, an octane improver such as tetraethyl lead, can and often does lower the cetane number of a diesel fuel.

U.S. Pat. No. 4,445,907 discloses the use of an amide containing an aminotetrazole group as a corrosion inhibitor for alcohol containing fuels such as gasohols. Likewise, U.S. Pat. No. 4,294,585 discloses the reaction product of an aminotetrazole, formaldehyde, and N-alkylpropylene diamine as a corrosion inhibitor for alcohol containing fuels.

The search has continued for various other compounds which can function as cetane improvers in diesel fuels. The present invention is a result of this search.

SUMMARY OF THE INVENTION

In one aspect of the present invention there is provided a liquid fuel adapted for use in a diesel engine containing a cetane number increasing amount of at least one fuel soluble additive compound represented by the structural formula:

wherein X represents a member selected from the group consisting of —O—, and >NR', and wherein R and R' independently are selected from the group consisting of hydrogen, alkyl, cycloalkyl, aryl, hydroxy, amino, alkoxy, hydroxyalkyl, aralkyl, and alkaryl.

In another aspect of the present invention, there is provided a process for improving the cetane member of a diesel fuel by incorporating at least one of the aforedescribed additives therein.

DESCRIPTION OF PREFERRED EMBODIMENTS

The cetane improver of the present invention is an organic compound which contains a five-membered diene hetrocyclic ring structure having four heteroatoms present therein, at least three of which heteroatoms are nitrogen, and which may be represented by the following structural formula:

wherein X represents a member selected from the group consisting of oxy (—O—), and >NR', and wherein R and R' independently are selected from the group consisting of hydrogen; alkyl, typically alkyl having from about 1 to about 200, preferably from about 1 to about 50, and most preferably from about 1 to about 10 carbons; cycloalkyl, typically cycloalkyl having from about 5 to about 12, preferably 6 to about 10, and most preferably about 7 to 9 carbons; aryl, typically aryl having from about 6 to about 14, preferably from about 6 to about 10, and most preferably about 6 carbons; amino >NH; hydroxy; alkoxy, typically alkoxy wherein the alkyl portion thereof is as described above in connection with alkyl; hydroxyalkyl; aralkyl or alkaryl wherein the respective alkyl, and aryl portions thereof are as described above.

Representative examples of suitable compounds included within structural formula I are:

1,2,3,4-tetraazacyclopenta-2,4-diene
5-methyl-1,2,3,4-tetraazacyclopenta-2,4-diene
5-propyl-1,2,3,4-tetraazacyclopenta-2,4-diene
5-hexyl-1,2,3,4-tetraazacyclopenta-2,4-diene
1,5-diethyl-1,2,3,4-tetraazacyclopenta-2,4-diene
1-benzyl-5-methyl-1,2,3,4-tetraazacyclopenta-2,4-diene
1-amino-5-propyl-1,2,3,4-tetraazacyclopenta-2,4-diene
1-methyl-5-hydroxy-1,2,3,4-tetraazacyclopenta-2,4-diene
5-ethoxy-1,2,3,4-tetraazacyclopenta-2,4-diene
1,5-dimethoxy-1,2,3,4-tetraazacyclopenta-2,4-diene
1,5-dihydroxy-1,2,3,4-tetraazacyclopenta-2,4-diene
5-amino-1,2,3,4-tetraazacyclopenta-2,4-diene
5-methyl-1-oxa-2,3,4-triazacyclopenta-2,4-diene
5-propyl-1-oxa-2,3,4-triazacyclopenta-2,4-diene
5-amino-1-oxa-2,3,4-triazacyclopenta-2,4-diene
5-benzyl-1-oxa-2,3,4-triazacyclopenta-2,4-diene
1-oxa-2,3,4-triazacyclopenta-2,4-diene
5-hydroxy-1-oxa-2,3,4-triazacyclopenta-2,4-diene
5-hexyl-1-oxa-2,3,4-triazacyclopenta-2,4-diene
5-propoxy-1-oxa-2,3,4-triazacyclopenta-2,4-diene
5-methoxy-1-oxa-2,3,4-triazacyclopenta-2,4-diene
5-cyclohexyl-1,2,3,4-tetraazacyclopenta-2,4-diene
5-hydroxyoctyl-1-oxa-2,3,4-triazacyclopenta-2,4-diene
5-ethylphenyl-1,2,3,4-tetraazacyclopenta-2,4-diene The preferred cetane improver is 5-propyl-1,2,3,4-tetraazacyclopenta-2,4-diene.

The compounds per se encompassed by structural formula I are well known and can be prepared by a variety of methods well known in the art. Representative synthesis routes are described in U.S. Pat. Nos. 1,943,148; 2,507,337; 2,977,372; and 3,437,665, and disclosures of which are herein incorporated by reference.

The amount of cetane improver added and dissolved in the fuel depends on the type of diesel fuel being used, the initial cetane value of the fuel, and the amount of cetane number increase desired. Accordingly, while any amount effective to increase the cetane number of the diesel fuel, relative to the absence of the additive, can be employed it is contemplated that such effective amount will constitute typically from about 0.001 to about 30, preferably from about 0.01 to about 1.0, and most preferably from about 0.05 to about 0.20%, by weight, based on the weight of the diesel fuel and additive.

Essentially, any hydrocarbon oil suitable as a fuel for diesel engines may be improved in the described manner. Ordinarily the hydrocarbon fuel to be used may be said to have a boiling range above that of gasoline, and, more particularly, the boiling range and viscosity of hydrocarbons present in a gas oil which boils from 400° to 700° F. Under some circumstances, a more narrowly cut fraction such as one distilling from about 400° or 450° to 600° F. may be used.

Thus, diesel fuels may be derived from crude oils, gas oils, and residual fuels having low pour points, low A.P.I. gravities and high heat values, such as those procured from naphthene base, asphalt base, or mixed base stocks.

Small quantities of the novel addition agents of this invention are useful for adapting various mixtures of hydrocarbons for use as diesel fuels, including recycle stocks from cracking operations, non-paraffinic extracts, distillates from the destructive distillations of coal and asphaltic materials, and mixtures of these with one another or with crude petroleum fractions.

Other agents for enhancing various other qualities without detracting substantially from the ignition qualities of the fuel may be admixed, such as oiliness agents, dyes, pour point depressants, viscosity modifiers, oxidation inhibitors and knock suppressing agents.

The following examples are given as specific illustrations of the claimed invention. It should be understood, however, that the invention is not limited to the specific details set forth in the examples. All parts and percentages in the examples as well as in the remainder of the specification are by weight unless otherwise specified.

EXAMPLE 1

The cetane increase caused by the present additives was measured in comparison to that caused by a commercial cetane improver 2-ethylhexylnitrate.

Accordingly, several samples of a base diesel fuel having a cetane number value of 41.0±1.2 were provided.

Then, 5-propyl-1,2,3,4,tetraazacyclopenta-2,4-diene (referred to herein as 5-propyltetrazole) was then synthesized as follows:

Butyronitrile (13.8 g, 0.20 mole), sodium azide (14.3 g, 0.22 mole), and ammonium chloride (0.5 g, 0.01 mole) were added to 100 ml of dimethylformamide. The mixture was heated at 120°–125° C. for 24 hrs. After cooling, the solvent was removed in vacuo. The residue was dissolved in 100 ml of water and extracted with toluene. After work-up, the 5-propyltetrazole was recrystallized from diethyl ether (mp 59°–64° C.).

Four base fuel samples were each treated with 500 ppm of the 5-propyltetrazole, and four other base fuel samples were each treated with 500 ppm of 2-ethylhexylnitrate.

The test samples were paired and rated in accordance with the ASTM D-613 test procedure and the results summarized at Table 1 below.

TABLE 1

| Run No. | Centane Number 5-propyltetrazole | 2-ethylhexylnitrate | Difference in cetane numbers |
|---|---|---|---|
| 1 | 43.8 | 43.8 | 0 |
| 2 | 42.5 | 42.0 | +0.5 |
| 3 | 44.3 | 43.4 | +0.9 |
| 4 | 43.4 | 42.4 | +1.0 |
| Average | 43.5 ± 1.2 | 42.9 ± 1.3 | +0.6 ± 7.7 |

As can be seen from Table 1, the 5-propyltetrazole is about 32% more potent than the commercial cetane improver 2-ethylhexylnitrate. This difference was statistically significant at the 95% confidence level.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A liquid fuel adapted for use in a diesel engine containing a cetane number increasing amount of at least one fuel soluble additive compound represented by the structural formula:

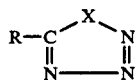

wherein X represents a member selected from the group consisting of —O—, and >NR', and wherein R and R' independently are selected from the group consisting of hydrogen, alkyl, cycloalkyl, aryl, hydroxy, amino, alkoxy, hydroxyalkyl, alkaryl, and aralkyl.

2. The fuel composition of claim 1 wherein the cetane number improving additive is 5-propyl-1,2,3,4-tetraazacyclopenta-2,4-diene.

3. The fuel composition of claim 1 wherein said fuel is a petroleum-derived distillate fuel.

4. The fuel composition of claim 1 wherein the cetane number improving additive is represented by structural formula I wherein X is >NH, and R is $C_1$ to $C_{10}$ alkyl.

5. A process for improving the cetane number of a liquid fuel adapted for use in a diesel engine which comprises admixing with said fuel a cetane number improving amount of at least one additive represented by the structural formula:

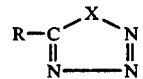

wherein X represents a member selected from the group consisting of —O—, and >NR', and wherein R and R' independently are selected from the group consisting of hydrogen, alkyl, cycloalkyl, aryl, hydroxy, amino, alkoxy, hydroxyalkyl, alkaryl and aralkyl.

6. The process of claim 5 wherein said additive is 5-propyl-1,2,3,4-tetraazacyclopenta-2,4-diene.

7. The process of claim 5 wherein in said structural formula X is >NH, and R is $C_1$ to $C_{10}$ alkyl.

* * * * *